United States Patent [19]
Gallagher

[11] Patent Number: 5,224,936
[45] Date of Patent: Jul. 6, 1993

[54] AUTOMATIC SELF-PROTECTING HYPODERMIC NEEDLE ASSEMBLY

[76] Inventor: Brian Gallagher, 2520 Crescent Rd., Homewood, Ill. 60430

[21] Appl. No.: 961,501

[22] Filed: Oct. 15, 1992

[51] Int. Cl.⁵ .............................................. A61M 5/32
[52] U.S. Cl. ................................... 604/192; 604/198; 604/145; 604/110
[58] Field of Search ................ 604/110, 187, 192, 198, 604/141–147, 263, 218

[56] References Cited

U.S. PATENT DOCUMENTS

| | | |
|---|---|---|
| Re. 25,279 | 10/1962 | Crockford et al. . |
| 3,055,362 | 9/1962 | Uytenbogaart .......... 604/144 |
| 3,134,380 | 5/1964 | Armao . |
| 4,031,889 | 6/1977 | Pike ........................ 604/144 |
| 4,725,267 | 2/1988 | Vaillancourt . |
| 4,795,432 | 1/1989 | Karczmer . |
| 4,846,809 | 7/1989 | Sims . |
| 4,892,521 | 1/1990 | Laico et al. . |
| 4,911,694 | 3/1990 | Dolan . |
| 4,915,696 | 4/1990 | Feimer . |
| 4,943,284 | 7/1990 | Erlich . |
| 4,986,819 | 1/1991 | Sobel . |
| 5,015,240 | 5/1991 | Zoltan et al. . |
| 5,026,353 | 6/1991 | Bartman .................. 604/192 |
| 5,059,180 | 10/1991 | McLees . |
| 5,167,641 | 12/1992 | Schmitz ............... 604/110 X |

*Primary Examiner*—John D. Yasko
*Attorney, Agent, or Firm*—Welsh & Katz, Ltd.

[57] ABSTRACT

An automatic self-protecting hypodermic needle assembly comprising a hypodermic syringe having a housing, a moveable plunger in the housing, a medicant chamber formed between the housing and the plunger, and a hollow needle extending from the housing in communication with the medicant chamber. A needle guard assembly is attached to the syringe housing and includes a guard housing adjacent the needle, a protective cap removably attached to the guard housing and an aperture through which the needle extends. A propellant is located in the guard housing in communication with the protective cap. When activated by an activating element, the propellant expands from a liquid to a gas, applies a pressure to the protective cap, and drives the protective cap along the length of the needle until the cap extends beyond the tip of the needle and the needle tip becomes embedded in the protective cap. Control means are provided under the operation of the medical attendant using the hypodermic syringe to automatically activate the propellant upon completion of the use of the syringe, and to embed the needle tip into the protective cap.

12 Claims, 4 Drawing Sheets

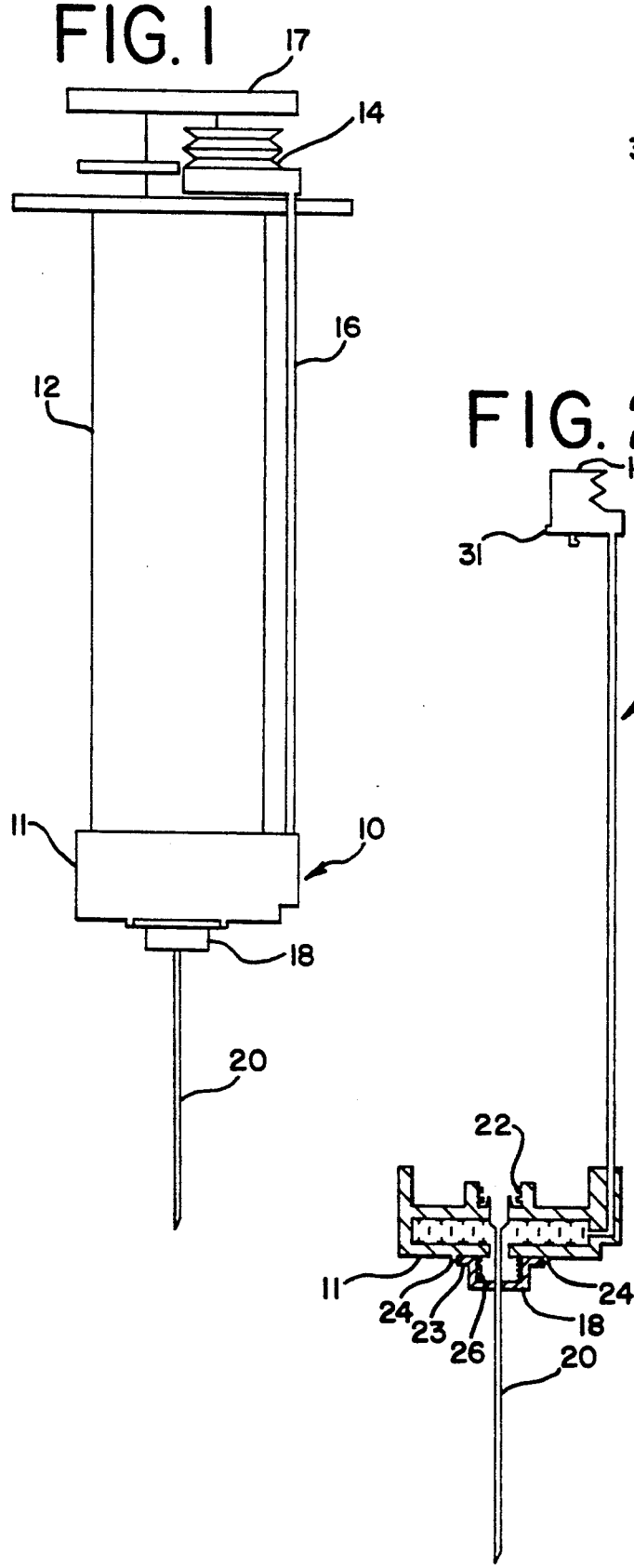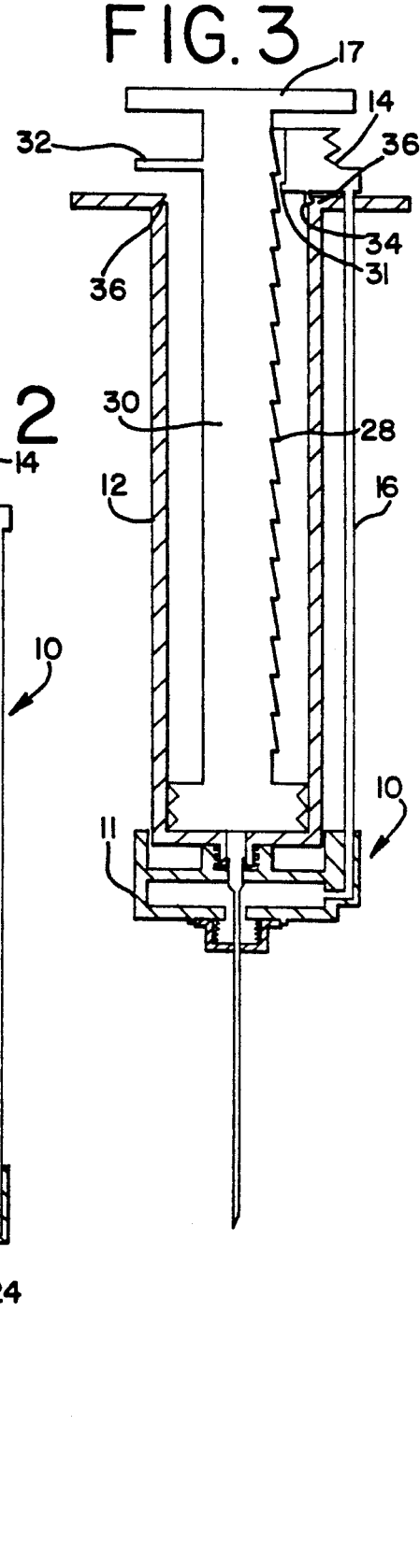

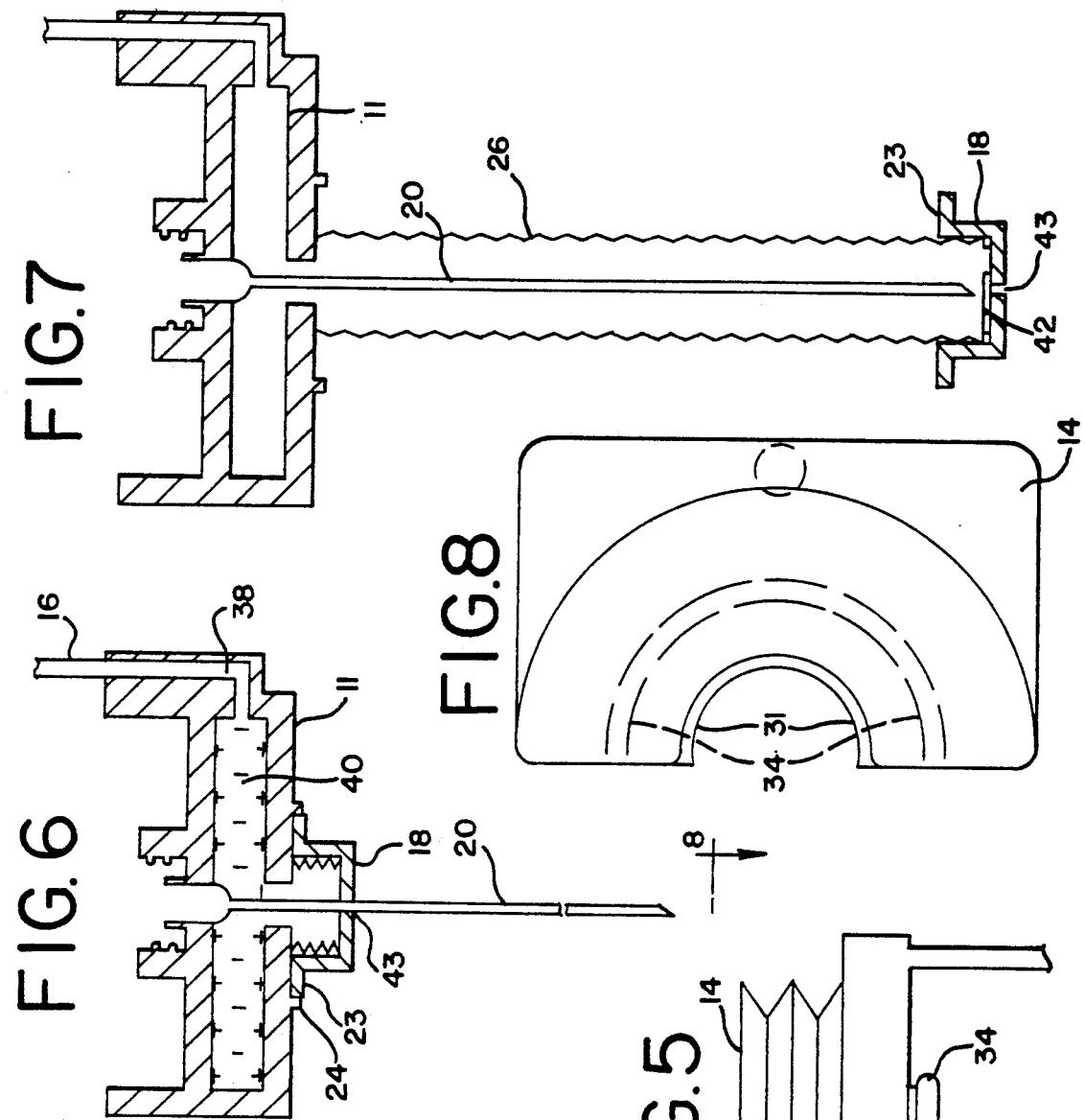

BEFORE

AFTER

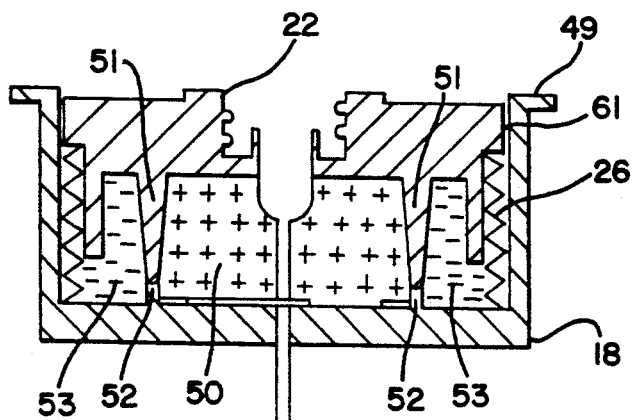
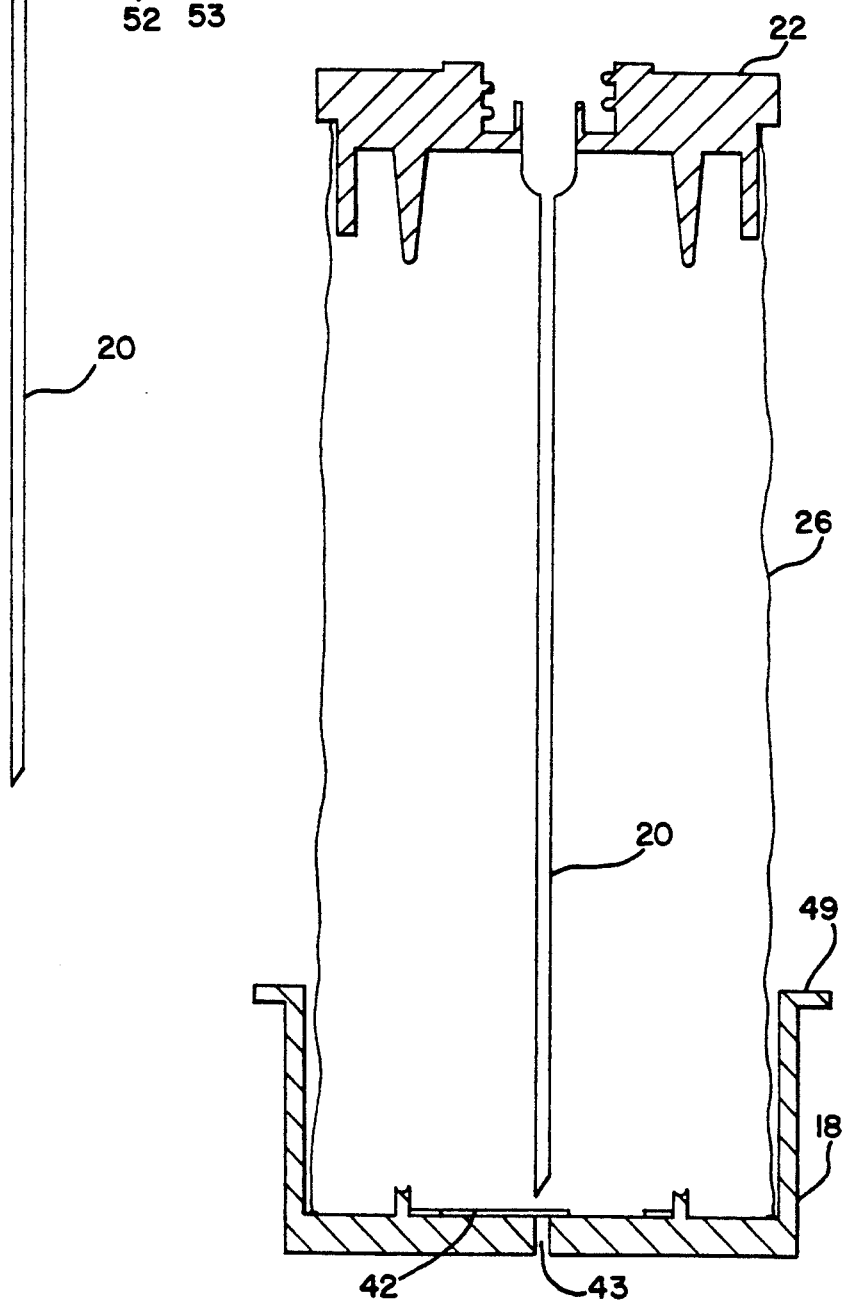

AUTOMATIC SELF-PROTECTING HYPODERMIC NEEDLE ASSEMBLY

The present invention relates to protective devices for hypodermic syringes to prevent the needle of the syringe from repuncturing the skin of the patient or health care professional after the intended use of the syringe, and more particularly to an automatically operated needle guard assembly which embeds the syringe needle into a protective cap to prevent repuncture after each use of the needle.

BACKGROUND OF THE INVENTION

Because of the possibility of spreading infectious disease, hypodermic needles used in the health care industry are generally disposed of after a single use. The need to prevent repuncture with used hypodermic needles has become of paramount importance in view of the AIDS epidemic. Patients, doctors, nurses, lab personnel, and hospital laundry workers have become accidentally infected with the AIDS HIV virus by puncturing themselves with hypodermic needles previously used on AIDS infected patients. Although provisions are made for the safe disposal of hypodermic needles in the medical workplace, the difficult and sometimes chaotic environment of some medical situations can cause even the best trained medical personnel to misplace a used hypodermic needle.

Because the hypodermic needle is frequently used during times of high stress, it would be of great benefit to provide a needle that automatically shields itself after a single use without the necessity of any conscious effort or thought by the attendant using the needle.

Many different protective cap-type, or sheath-type devices for protecting hypodermic needles against accidental needle sticks have been advanced. While many of these devices are workable, they either require manual deployment of a protective cap or sheath, (and thus a conscious effort by the attendant) or they involve a mechanism that obstructs the attendant's view of the needle as it is advanced into the patient's skin. Other shielding devices that are available involve complex mechanisms which would be costly to manufacture. U.S. Pat. No. 4,915,696 to Feimer, U.S. Pat. No. 4,725,267 to Vaillancourt, U.S. Pat. No. 4,986,819 to Sobel, U.S. Pat. No. 4,892,521 to Laico, U.S. Pat. No. 4,846,809 to Sims U.S. Pat. No. 4,943,284 to Erlich, U.S. Pat. No. 4,911,694 to Dolan, and U.S. Pat. No. 5,015,240 to Soproni are representative of devices which require manual deployment of a trigger, or of a protective cap or sheath by the attendant. These devices do not address the need for automatic actuation of the cap to eliminate the element of human error in deployment of the protective device.

Some prior inventions obstruct the vision of a substantial portion of the needle when entering the patient's skin, and require a specific amount of insertion into the skin to effect the triggering of the protective device, (e.g. U.S. Pat. No. 4,795,432 to Karczmer and U.S. Pat. No. 5,059,180 to McLees). These type of devices would be inconvenient to use and deploy, and possibly dangerous.

It is an object, therefore, of the present invention to provide a needle tip protective guard for a hypodermic needle that operates automatically and that requires no additional action by the operator.

It is another object of the invention to provide a needle guard having a short, unobtrusive profile in the retracted, inactivated position.

It is a further object of the invention to provide a needle tip guard which includes a propellent system for placing the guard, which propellent system becomes activated when the operator presses the plunger on the hypodermic syringe to complete the injection. Thus, the act of using the syringe causes the guard to operate.

It is another object to provide a needle guard that will close itself off to prohibit the needle from reemerging once it has been enclosed by the guard.

Another object is to provide a needle guard that is made integral with the needle, so that the needle and guard are mounted to the syringe simultaneously.

A still further object of the invention is to provide such a guard mechanism that is constructed of simple plastic parts to minimize material and production costs.

SUMMARY OF THE INVENTION

These and other objects of the invention are achieved by a mechanism that uses gas pressure produced by the combining of two chemicals to propel a protective cap along the needle shaft and over the needle tip. The two chemicals are combined when the attendant pushes the syringe to inject medication into the patient, and, in a first embodiment, simultaneously squeezes a small bellows located under the plunger. The bellows pumps a liquid chemical through a tube and into contact with another chemical located in a chamber at the hub of the needle. In a second embodiment, the attendant depresses a circular disc and push rod assembly simultaneously with the syringe plunger to cause communication between the two chemicals in the chamber. The chamber in both embodiments is connected to a flexible sheath that is in an initially collapsed configuration. A plastic cap with a small aperture through which the needle protrudes is connected to the other end of the flexible sheath. A slow progressive gas pressure results from the chemical reaction in the chamber causing the flexible sheath to elongate and push the protective cap down the needle shaft and over into contact with the tip. The protective cap contains a plastic wafer with a small moveable tab member in its center that is elastically biased toward the center, but held aside by the needle. When the needle tip is withdrawn from the aperture in the cap, the moveable tab member returns to center, blocks the aperture, and prohibits the needle from reemerging from the protective cap.

Other objects and features of the invention will become apparent from the following detailed description of the preferred embodiments when taken in conjunction with the drawings wherein reference to specific parts is made.

BRIEF DESCRIPTION OF THE DRAWINGS

FIG. 1 is an elevation view of a hypodermic needle equipped with the automatic needle guard.

FIG. 2 is a partial cross section elevation view of the needle guard assembly of FIG. 1 before being attached to the syringe.

FIG. 3 is a side cross section view of the hypodermic needle with the automatic needle guard ready to draw medication into the syringe.

FIG. 4 is a side cross section view of the hypodermic needle with the automatic needle guard, wherein the needle is ready to inject medication into the patient.

FIG. 5 is a cut-away side view of the top portion of the needle guard assembly of FIG. 2 showing the bellows pump.

FIG. 6 is a cut-away, cross section view of the bottom portion of the needle guard assembly of FIG. 2, showing the hypodermic needle and the automatic needle guard. I FIG. 7 illustrates the needle guard of FIG. 6 fully expanded with the needle enclosed within the protective cap.

FIG. 8 is a top view of the bellows pump and its mounting element, taken along line 8—8 of FIG. 5.

FIG. 13 is a detail, cross section view of the embodiment of FIG. 11 showing the hypodermic needle and the interior structure of the automatic needle guard.

FIG. 14 is an elevation cross section view of the needle guard of the embodiment of FIG. 11 shown in the fully extended position with the needle enclosed within the protective cap.

DETAILED DESCRIPTION OF THE PREFERRED EMBODIMENTS

Figure 9:
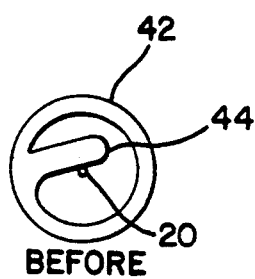
FIGS. 9 & 10 are end views of the plastic wafer forming part of the needle guard assembly, showing the position of the moveable member before and after the needle is enclosed within the protective cap.

For the sake of brevity, like components shall have the same designation throughout the description of the figures.

Referring to FIG. 1, a plastic needle guard chamber assembly 10 is attached to the needle end of hypodermic syringe 12 by the twist-on method used on conventional needles. A liquid carrying tube 16 is made integrally with, and shown connected to a guard housing 11 at one end, and at the other end tube 16 is connected to a bellows type pump 14 located under the syringe plunger 17. The hypodermic needle 20 is made integrally with the needle guard housing 11 and is shown in a fully exposed position with a moveable protective cap 18 in an unactivated position.

In FIG. 2, the needle guard chamber assembly 10 described above is shown in condition for attachment to the syringe 12. A conventional needle 20 and internally threaded hub 22 are shown relative to the other needle guard chamber assembly components. The protective cap 18 is shown secured to the needle guard housing 11 by a friction hold created between flanges 23 of cap 18 and the inside of a shallow socket 24 depending from housing 11. The cap 18 may also be secured by adhesive, or other suitable means. The protective cap 18 has contained within it an expandable sheath 26 made of a resilient material such as latex or plastic. The sheath 26 is connected to the protective cap 18 at one end and to the needle guard chamber 11 at the other end.

In FIG. 3, the assembly depicted in FIG. 2 is shown connected to a hypodermic syringe 12 which is ready to draw medication. The syringe plunger 17, which can be freely rotated axially within the syringe, is shown with ratchet type serration 28 along the length of the syringe stem 30 and extending half way around the circumference of stem 30. The bellows pump 14 is shown with a molded step 31 which acts as a pawl in conjunction with the serration 28 on the syringe plunger stem 30. Also on the syringe stem 30 is a low profile, cantilevered radial extension 32 which encircles 180 degrees of the stem opposite to the extension of the serration 28. Extension 32 provides a bellows pump contact between the bellows 14 and the stem 30. The serrations 28 allow for retraction of the plunger when drawing medication from a vial, but prohibit advancement of the plunger. After the attendant fills the syringe, the plunger is rotated 180 degrees to simultaneously disengage the serration 28 from the pawl 31 and to place the extension 32 directly over the bellows pump 14.

In FIG. 4, the plunger 17 has been rotated 180 degrees from its previous position shown in FIG. 3 and lifted upward, whereby the device is ready to inject medication into the patient. As plunger 17 is lowered, the bellows pump conductor or extension 32 begins to depress the bellows pump 14 in the final ⅛ to ¼ inch of travel as the syringe plunger 17 is pushed by the attendant to inject medication through hollow tube 20. After injection, the bellows pump 14 will have forced a quantity of liquid material or chemical contained therein to travel into tube 16 and then into guard housing 11, as will be described.

In FIGS. 5 & 8, the bellows pump 14 is shown with a rounded bead 34 at its lower end which snaps into a mating groove 36 (shown in FIG. 3) in the top of the syringe housing. These mating parts provide for quick and simple snap-on mounting of the bellows pump 14 to the syringe 12. Also shown is the pawl 31 encircling 180 degrees of the inside of the bellows pump.

FIG. 6 shows the tube 16 connected to the guard housing 11. The housing 11 includes a hollow portion 40 in which a first chemical propellent is disposed. A second liquid chemical is disposed in bellows pump 14 and tube 16. The first and second chemicals in hollow portion 40 and tube 16, respectively, are reactants relative to each other, whereby when the two chemicals come into contact, a reaction results, producing a gaseous product of reaction and an increase in the pressure in hollow portion 40 of housing 11. To prevent premature contact of the two chemical reactants, a small amount of viscous fluid 38 such as petroleum jelly or similar thick material acts as a plug in tube 16 at its entrance to the housing 11. The gas producing reactants may be any compounds or combination or solutions of compounds that when combined, will produce emission of gas. Such compounds could be water plus a mixture of citric acid and sodium carbonate, hydrogen peroxide and manganese dioxide, acetic acid and sodium bicarbonate, or similar known materials.

The gas produced by combining the chemical reactants will cause an increase in pressure within the hollow portion 40 of guard housing 11. This pressure acts upon the upper surface of protective cap 18, dislodging the protective cap and flange 23 from socket 24, and forcing the protective cap downward along the length of needle 20. As shown in FIG. 7, expandable sheath 26 extends downward along protective cap 18, forming an extension of pressurized chamber portion 40, thereby maintaining the gaseous pressure against protective cap 18.

FIG. 7 shows the sheath 26 fully expanded with the protective cap 18 moved to a position beyond the tip of the hypodermic needle 20. Also shown in FIG. 7 is a thin wafer 42 lodged in protective cap 18. The wafer 42 includes a flexible tab 44 (FIGS. 9 & 10) which, in one position covers the aperture 43 in the protective cap. The tab 44 seals the aperture 43 in the protective cap 18 to prevent the needle 20 from reemerging from the cap.

Figure 10:
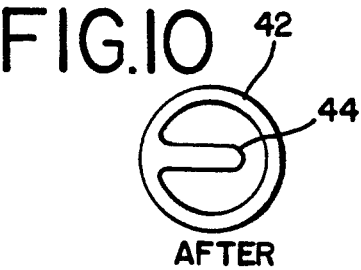

FIGS. 9 & 10 are detailed illustrations of the thin plastic wafer 42, shown in FIG. 9 with the needle 20 holding the wafer's moveable member 44 to the side. When protective cap 18 is extended by gas pressure beyond the tip of needle 20, the needle is withdrawn from the aperture 43 in the protective cap 18, the moveable tab member 44 is allowed to return to center by its own resiliency (as shown in FIG. 10) and the tab blocks the needle 20 from reemerging from the protective cap 18 through aperture 43.

In operation, the medical professional attaches the needle guard assembly 10 (as shown in FIG. 2) to the hypodermic syringe 12 by threading the needle guard housing 11 onto the hypodermic syringe. The bellows pump 14 is then snapped onto the top of the syringe and held in place by a snap-fit of the rounded bead 34 on the bellows 14 and the mating groove 36 on the syringe 12. The attendant then inserts the hypodermic needle 20 into a vial of medication, and lifts the plunger 17 until the required amount of medication has entered the syringe 12. The needle is then removed from the vial and the plunger 17 is rotated 180 degrees to simultaneously disengage the serration 28 from the pawl 31, and to place the conductor extension 32 over the bellows pump 14.

The attendant then inserts the needle 20 into the patient's skin and presses the plunger 17 to inject the medication. In the final ⅛ to ¼ inch of travel of the plunger 17, the conductor 32 compresses the bellows pump 14 and displaces a quantity of liquid Chemical down through tube 16 and into chamber 40, dislodging viscous liquid 38 whereby the first liquid in tube 16 comes into contact with the second chemical in chamber 40. After completion of the injection, the needle 20 is withdrawn from the patient as the chemical reaction continues inside the chamber 40. A steadily increasing pressure develops as the chemical reaction inside the chamber 40 produces gas. The gas pressure causes the protective cap 18 to be propelled down the needle 20 and expandable sheath 26 to elongate under the force of the gas pressure. When the protective cap 18 has moved completely over the end of the needle 20, the tab member 44 (FIG. 10) closes off the aperture 43 in the protective cap 18 to prevent reemergence of the hypodermic needle 20 through the aperture 43.

The needle guard assembly 10' constructed according to a second embodiment of the invention will now be described with reference to FIGS. 11-14. In this embodiment, the mechanism for triggering the chemical reaction to propel the protective cap 18 is different from the embodiment of FIGS. 1-10.

Figure 11:
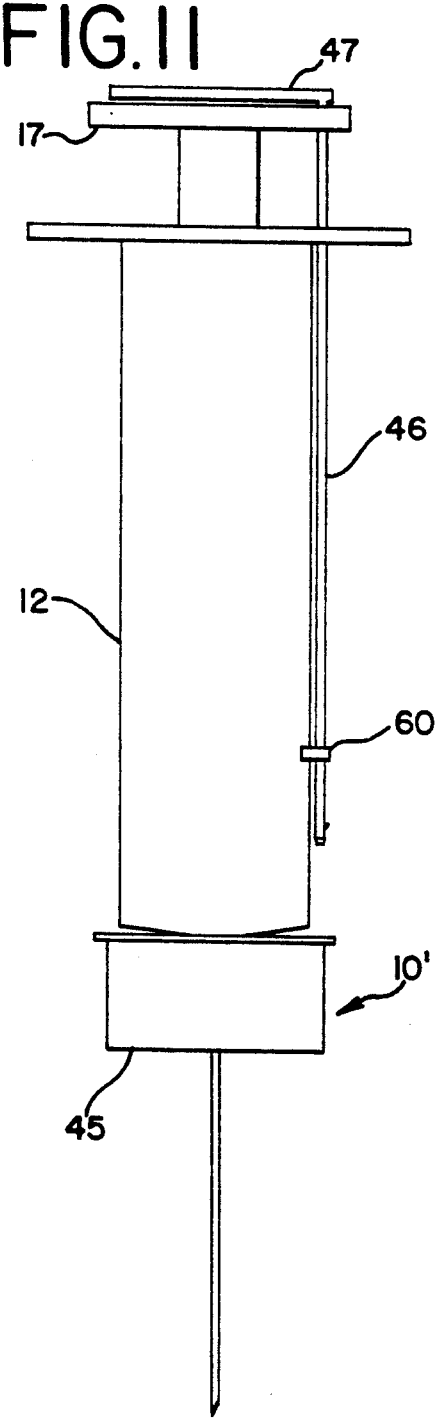
FIG. 11 is an elevation view of an alternate embodiment of the present invention.

In FIG. 11 the hypodermic syringe 12 is shown connected to the needle guard assembly housing 45. A push rod 46 slidably extends through a bracket 60 which is mounted alongside of the syringe 12. The push rod 46 has a circular disc 47 at the upper end that extends over the top of the syringe plunger 17.

Figure 12:
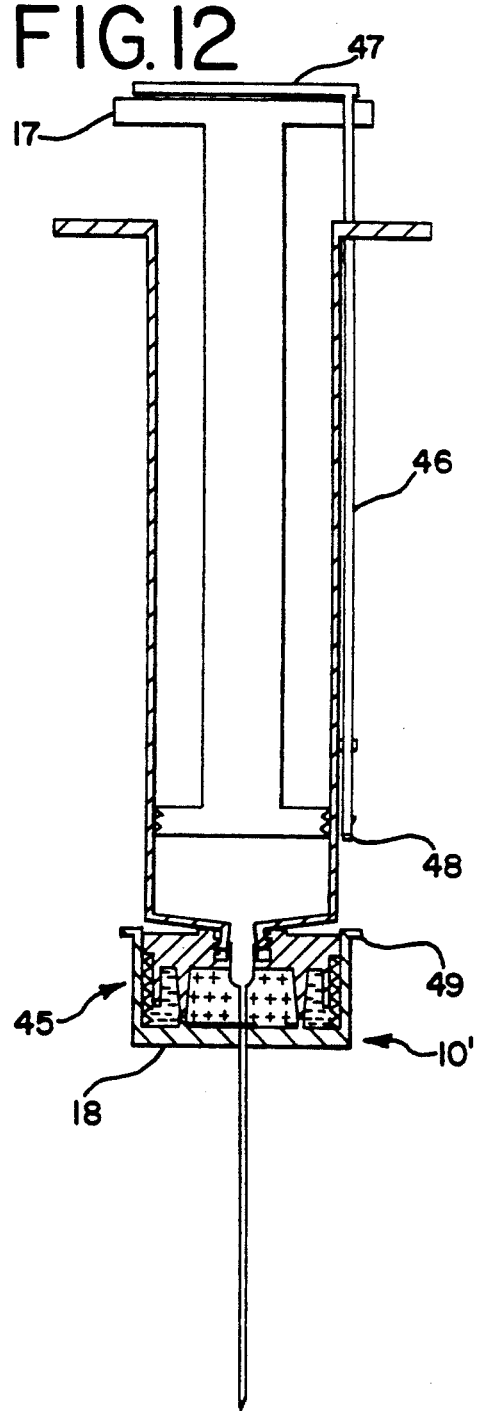
FIG. 12 is an elevational cross section view of the embodiment of FIG. 11 showing the needle guard assembly attached to the syringe.

FIG. 12 shows the device of the second embodiment in condition to inject medication into the patient. The attendant presses the circular disc 47 and the syringe plunger 17 downward simultaneously to administer the injection. The end 48 of push rod 46 moves downward and contacts a flange 49 on the protective cap 18 in the final ⅛ inch of travel of the syringe plunger 17. In this embodiment, the side of the protective cap 18 extends upward alongside hub 22, and is releasably and frictionally held to hub 22 at 61 (FIG. 13). When the injection is completed, the push rod will have advanced the protective cap 18 approximately ⅛ of an inch downward and the chemicals located within the protective cap 18, as will be described, will combine and produce gas, applying a downward pressure on cap 18.

FIG. 13 is a detail view of the interior of protective cap 18, and shows the threaded hub 22 for mounting the needle 20 to the syringe 12. The expandable sheath 26 is shown connected to the hub 22 at the top and to the protective cap 18 at the bottom. Two chemical reactants 50 and 53 are located within the protective cap 18, and are initially separated by a cylindrically shaped flange 51 that extends downwardly from hub 22. Flange 51 is in mating contact with a corresponding flange 52 which extends upward from the bottom interior of protective cap 18. When the protective cap 18 has been advanced slightly by the downward movement of push rod 46 after completion of the injection, the mating flanges 51 and 52 separate to allow communication between the two chemical reactants 50 and 53. The gas produced by the chemical reaction will cause an increase in pressure inside the protective cap 18, and an elongation of the expandable sheath 26 along with downward movement of protective cap 18. FIG. 14 shows the sheath 26 fully expanded with the protective cap 18 covering the tip of the hypodermic needle 20. Also shown is tab 42 covering the aperture 43 in the protective cap as described in conjunction with the first embodiment. As in the first embodiment, the tab 42 prevents the needle 20 from reemerging from the protective cap 18.

In operation, the medical professional attaches the needle guard assembly 45 to the hypodermic syringe 12 by threading the needle guard chamber hub 22 onto the mating thread on the hypodermic syringe. The attendant then inserts the hypodermic needle 20 into a vial of medication and retracts the plunger 17 until the required amount of medication has entered the syringe 12. The needle 20 is then removed from the vial, and the syringe is ready to inject medication. The attendant inserts the needle 20 into the patient's skin and presses downward on the circular disc 47 and the syringe plunger 17 simultaneously. In the final ⅛ to ¼ inch of travel of the syringe plunger 17, the push rod 46, which is connected to the circular disc 47, contacts flange 49 on the protective cap 18, and moves the protective cap a short distance down the needle 20. The short displacement of the protective cap 18 separates flanges 51 and 52 (FIG. 13), which allows communication between chemicals 50 and 53. This starts a chemical reaction within the protective cap 18 just as the injection is completed and the needle is removed from the patient's skin.

The chemical reaction described above is started when the protective cap 18 is displaced a short distance causing separation of the downward extending flange 51 from a mating upwardly extending flange 52. This separation of flanges 51 and 52 causes the liquid chemical reactant 53 to come into contact with the other chemical reactant 50. A few seconds after the injection is completed, an increasing gas pressure develops inside the protective cap 18 as the chemical reaction progresses. The gas causes the expandable sheath 26 to elongate and the protective cap 18 to move down the needle 20. When the protective cap 18 has moved completely over the end of the needle 20, the tab member 42 closes off the aperture 43 in the protective cap 18 to prevent reemergence of the needle 20.

Specific embodiments of the novel Automatic Self-Protecting Hypodermic Needle Assembly according to the present invention have been described for the purpose of illustrating the manner in which the invention may be made and used. It should be understood that implementation of other variations and modifications of the invention in its various aspects will be apparent to those skilled in the art and that the invention is not limited by the specific embodiments described. It is therefore contemplated to cover by the present invention any and all modifications, variations, or equivalents that fall within the true spirit and scope of the basic underlying principles encompassed by the claims set forth hereinbelow.

I claim:

1. An automatic self-protecting hypodermic needle assembly comprising:
   a hypodermic syringe including a housing, a moveable plunger in said housing, a medicant chamber formed between said housing and said plunger, and a hollow needle extending from said housing, said hollow needle in communication with said medicant chamber and having a tip at a distal end of said needle;
   a needle guard assembly attached to said syringe housing, said needle guard assembly including:
   a guard housing disposed adjacent said needle;
   protective cap means removeably attached to said guard housing, said protective cap means having an aperture therethrough, said needle extending through said aperture;
   said guard housing having propellant means disposed therein in communication with said protective cap means, said propellant means includes a first chemical propellant means which, when activated, expands and applies a pressure to said protective cap means;
   activating means in selective communication with said propellant means to selectively activate said first chemical propellant when said activating means comes into contact with said first chemical propellant means; and
   control means in communication with said activating means and actuated by depression of said plunger to activate said first chemical propellant means and produce a pressure which dislodges said protective cap means from said guard housing and moves said protective cap means along the length of said needle until said protective cap means engages the tip of said needle and said needle tip becomes embedded in said protective cap means.

2. The automatic self-protecting hypodermic needle assembly of claim 1 wherein said guard housing includes a propellant chamber in which said first chemical propellant means is disposed, which first chemical propellant means pressurizes said propellant chamber when activated to apply said pressure and to dislodge said protective cap means.

3. The automatic self-protecting hypodermic needle assembly of claim 2 wherein said control means includes a bellows disposed on said syringe housing such that a portion of said plunger actuates said bellows when said plunger is depressed into said syringe housing a predetermined amount.

4. The automatic self-protecting hypodermic needle assembly of claim 3 including tube means communicating between said bellows and said propellent chamber, said activating means including a second chemical activator means disposed in said tube means which when coming into contact with said first chemical propellant in said propellant chamber causes a reaction with said first chemical propellant resulting in said pressurization of said propellant chamber and dislodging of said protective cap means.

5. The automatic self-protecting hypodermic needle assembly of claim 4 including a dislodgable substance disposed in said tube means separating said first chemical propellant means and said second chemical activator means until said bellows is actuated by said plunger.

6. The automatic self-protecting hypodermic needle assembly of claim 4 wherein said one of said first chemical propellant means and said second chemical activator means is selected from the group consisting of a mixture of citric acid and sodium carbonate, a mixture of hydrogen peroxide and manganese dioxide, and a mixture of acetic acid and sodium bicarbonate.

7. The automatic self-protecting hypodermic needle assembly of claim 6 wherein said second chemical activator means is water.

8. The automatic self-protecting hypodermic needle assembly of claim 5 wherein said dislodgable substance is selected from the group consisting of petroleum jelly and wax.

9. The automatic self-protecting hypodermic needle assembly of claim 1 wherein said protective cap means includes flexible needle sealing means therein, said flexible needle sealing means held in a first position away from said aperture in said protective cap means by said needle when said protective cap is attached to said guard housing and when said protective cap advances along the length of said needle;
   said flexible needle sealing means movable to a second position sealing said aperture in said cap means against reemergence of said needle when said protective cap means advances beyond the tip of said needle.

10. The automatic self-protecting hypodermic needle assembly of claim 1 wherein said control means includes a rod extending from a manually operated disc adjacent said plunger, said rod having an end thereof adapted to engage a flange on said protective cap means upon actuation of said control means to dislodge said protective cap means from said guard housing causing communication between said first chemical propellant means and said activating means.

11. The automatic self-protecting hypodermic needle assembly of claim 1 wherein a first chamber and a second chamber are located between said guard housing and said protective cap means, said first chamber and second chamber being separated by flange means extending between said first and second chambers, said first chemical propellant means disposed in one of said first and second chambers, said activating means disposed in the other of said first and second chambers, said control means adapted to break said flange means causing communication between said first chemical propellant means and said activating means.

12. The automatic self-protecting hypodermic needle assembly of claim 11 wherein said flange means includes a first portion connected and extending downward from said guard housing and a second portion connected to and extending upward from said protective cap means, said first and second portions of said flange means being in mating relationship to separate said first and second chambers until said control means dislodges said protective cap means.

* * * * *